United States Patent [19]
Mita et al.

[11] 3,971,828
[45] July 27, 1976

[54] N-(MERCAPTOACYL)AMINOACIDS

[75] Inventors: Itaru Mita, Ashiya; Shigeo Okumura, Takarazuka; Shigeru Yamabe, Kobe; Yoshihiko Funae, Suita; Junzo Matumoto, Osaka, all of Japan

[73] Assignee: Santen Pharmaceutical Co. Ltd., Osaka, Japan

[22] Filed: Dec. 23, 1974

[21] Appl. No.: 535,686

Related U.S. Application Data

[62] Division of Ser. No. 398,934, Sept. 20, 1973, Pat. No. 3,897,480.

[30] Foreign Application Priority Data
Oct. 3, 1972    Japan.............................. 47-110491
May 11, 1973   Japan.............................. 48-52924

[52] U.S. Cl............................. 260/534 S; 260/516; 260/534 C; 424/319
[51] Int. Cl.[2].................................... C07C 149/243
[58] Field of Search...................... 260/534 C, 534 S

[56] References Cited
UNITED STATES PATENTS
3,246,025    4/1966    Mita et al.................... 260/534 S X FOREIGN PATENTS OR APPLICATIONS
1,023,003    3/1966    United Kingdom ................... 534 S/

OTHER PUBLICATIONS

Vasilevskii et al., J. Org. Chem. USSR, vol. 6 (1971) pp. 236–241.

Primary Examiner—Richard L. Raymond
Attorney, Agent, or Firm—Flynn & Frishauf

[57] ABSTRACT

Compounds useful for prophylaxis and therapy in treating a metabolic disorder, such as nosotoxicosis due to a heavy metal radiation disorder, diabetes or hepatitis.

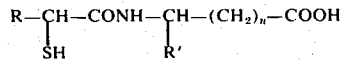

and intermediates therefor are disclosed.

2 Claims, No Drawings

N-(MERCAPTOACYL)AMINOACIDS

This is a division, of application serial number 398,934, filed Sept. 20, 1973, now U.S. Pat. No. 3,897,480.

This invention relates to novel N-(mercaptoacyl) aminoacids and intermediates therefor. Among N-(mercaptoacyl) aminoacids, we have already found 2-mercaptopropionylglyine and 3-mercaptopropionylglycine as compounds having excellent pharmacological activities (U.S. Pat. No. 3,246,025 and British Pat. No. 1,023,003).

We have continued the study as to various N-(mercaptoacyl) aminoacids thereby finding some compounds having pharmacological activities superior to those of the compounds which had been developed. In particular, this invention relates to compounds represented by the formula

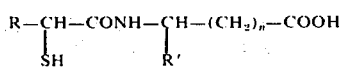

to human body such as a free radical or a peroxide and an accelerating action of metabolism, but also are low in toxity and have a high transitivity into tissue. These compounds are, therefore, useful for prophylaxis and therapy in treating a metabolic disorder such as nosotoxicosis due to a heavy metal, radiation disorder, diabetes or hepatitis. This invention provides an industrially convenient process for preparing these useful compounds.

The transitivity into tissue and the radioresisting action as to each resisting action were indicated as percent survival of mice and partition coefficient, respectively. The percent survival of mice was determined by use of fluorescence X-ray as follows.

The known compound, 2-mercaptopropionylglycine was used in this test as control. The mice were divided into groups of 30 mice each. The members of groups were administered with test compounds in the dose indicated, respectively. After the administration, the mice were irradiated with fluorescence X-ray to give the total dose of 800R as γ-rays and 30 days after the irradiation, the number of surviving mice was counted. The test results are shown in the following table.

Table

| Test Compounds | Percent of mice surviving 30 days after the γ-ray-irradiation for the total dose of 800R | Dose (mg/kg) | Partition coefficient (Butanol/Buffer,pH 7.4) |
| --- | --- | --- | --- |
| None | 17.1 | | |
| N-(2-mercaptopropionyl)-glycine | 43.0 | (20) | 0.17 |
|  | 31.0 | (10) | |
| N-(2-mercaptoisovaleryl)-glycine | 20.0 | (10) | 0.92 |
| N-(2-mercaptopheynylacetyl)-glycine | 54.5 | (10) | 1.03 |
|  | 31.5 | (5) | |
| N-(2-mercaptophenyl-propionyl) glycine | 51.5 | (10) | 2.54 |
|  | 25.7 | (5) | |
| N-(2-mercapto-p-chloro-phenylacetyl) glycine | 11.4 | (10) | 3.98 |
| N-(2-mercaptopropionyl-β-alanine) | 48.0 | (10) | 0.21 |
| N-(2-mercaptopropionyl)-leucine | 24.0 | (10) | 1.88 |
| N-(2-mercaptopropionyl)-5-aminocaproic acid) | 60.0 | (10) | 0.63 |
| N-(2-mercaptopropionyl)-phenylglycine | 46.0 | (10) | 1.73 |
| N-(2-mercaptopropionyl)-phenylalanine      H* | 52.0 | (10) | 3.68 |
| 2-mercaptopropionyl-phenylalanine      L* | 48.0 | (10) | 3.55 |

*H and L indicate diastereomers having a high melting point and a low melting point, respectively, which may be prepared in accordance with Examle VI hereinbelow.

wherein R is a member selected from the group consisting of alkyl, aryl and aralkyl radicals; R' is a member selected from the group consisting of a hydrogen atom and alkyl, aryl and aralkyl radicals and $n$ is an integer of from 0 to 4; when $n$ is an integer of from 1 to 4, R and R' being $CH_3$ and H respectively; when $n$ is zero, R being $CH_3$ and R' being a member selected from the group consisting of $CH_3$, $C_6H_5$, $C_6H_5CH_2$ and $(CH_3)_2CHCH_2$, or R being a member selected from the group consisting of $(CH_3)_2CH$, $C_6H_5$, p—Cl—$C_6H_4$ and $C_6H_5CH_2$ and R' being H.

Compounds of this invention have not been disclosed in any literature and are useful as therapeutic agents having various pharmacological activities. Namely, these compounds not only have an accelerating action for elimination of a heavy metal such as mercury, an eliminating action with respect to a substance harmful The compounds of this invention may be prepared by various known processes, but the following process is the most convenient because it gives the highest yield.

This process comprises reacting a compound represented by the formula

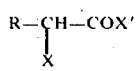

with a compound represented by the formula

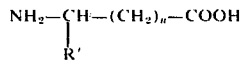

in a solvent in the presence of an alkaline agent to form a compound represented by the formula

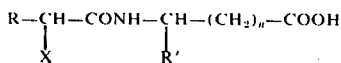

reacting the compound with a salt of thiobenzoic acid or xanthogenic acid to form a compound represented by the formula

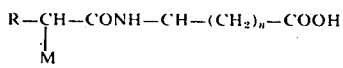

and subjecting the compound to hydrolysis. In the above formulae, R, R' and n are as defined above; X and X' are independently a halogen atom; and M is a thiobenzoic acid or ethylxanthogenic acid residue.

Examples of the alkaline agent are hydroxides, carbonates of sodium and potassium and ter.-amine salts such as pyridine and triethylamine salts and the like. The reaction of the halide with the aminoacid in the presence of an alkali is conveniently carried out in a solvent such as water, ether, benzene, chloroform, acetone, dioxane at a low temperature while maintaining the pH of the reaction mixture at neutral or slight alkalinity.

The resulting compound represented by the formula

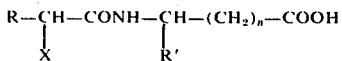

was optionally isolated and reacted with a salt of thiobenzoic acid or alkylxanthogenic acid in water or a proper organic solvent, for example, a lower alcohol or ethyl acetate at a low temperature to give an S-substituted compound. This compound may be subjected to hydrolysis with the aid of a hydroxide of alkali metal, alkaline earth metal or ammonia in water or in a lower alcohol at room temperature or an elevated temperature to disconnect the substituent. The N-(2-mercaptoacyl) aminoacid thus obtained may be readily purified by recrystallization from an organic solvent such as ethyl acetate.

The present invention is further illustrated by the following examples, but they are not to be construed as limiting the present invention.

EXAMPLE I 200 ml of thionylchloride was added to 62.9g (0.293 mol) of α-bromophenylacetic acid and the resulting mixture was refluxed for 2 hours. After the completion of the reaction, excess thionylchloride was removed from the reaction mixture under reduced pressure and then the reaction mixture was distilled to yield 62.8g of 2-bromophenylacetic chloride (b.p. 105°C/5 mmHg).

Then, 7.5g (0.10 mol) of glycine was neutralized with 50 ml of 2N—NaOH and to the resulting solution were added dropwise over 1 hour 20.0g (0.085 mol) of 2-bromophenylacetylchloride and 43 ml of 2N—NaOH while stirring. During the addition, the reaction mixture was maintained at a temperature below 5°C and adjusted to a pH of about 8. After the completion of the addition, the mixture was stirred at room temperature for 4 hours to complete the reaction. To the resulting solution, without isolating a bromine-containing compound, was added the filtrate which had been prepared by neutralizing 13.8g (0.10 mol) of thiobenzoic acid with 50 ml of 2N-KOH and the thus obtained solution was filtrated to remove undissolved substances, and then the mixture was allowed to stand overnight at room temperature while adjusting the pH to about 8. On the next morning, the solution was acidified with hydrochloric acid while ice-cooling to precipitate crystals. The crystals were recovered by filtration, washed with water, dried and recrystallized from benzene to give 23.9g of 2-benzoylmercaptophenylacetylglycine as white crystals (m.p. 133-138°C).

9.9g (0.03 mol) of the 2-benzoylmercaptophenyacetylglycine was added to 50 ml of concentrated aqueous ammonia and the mixture was stirred at room temperature for one hour. During stirring and about 30 minutes after the addition, the formation of benzamide was observed. After the completion of the reaction, the benzamide was removed by extraction with ether. After removing the ammonia under reduced pressure, the aqueous layer was acidified with hydrochloric acid and extracted with ethyl acetate. The extract was washed with water and dried over anhydrous sodium sulfate. After the ethyl acetate had been distilled off, a small amount of benzene was added to the extract to give N-(2-mercaptophenylacetyl)glycine, $C_6H_5CH(SH)CONHCH_2COOH$, as white crystals. Yield; 5.6g, (m.p. 91°– 93°C).

Infrared Spectrum:
3260 cm$^{-1}$ (—NH—); 1760 cm$^{-1}$ (—COOH);
1610 cm$^{-1}$, 1150 cm$^{-1}$ (—CONH—)

EXAMPLE II 2.9g of the bromine-containing compound prepared by the method according to Example I was neutralized with an alkali and then 2.4g (1.5 times mol as great as that of the compound) of potassium ethylxanthogenate was added to the neutralized compound followed by stirring at room temperature overnight. The next morning, the reaction mixture was acidified with hydrochloric acid to give 3.3g of N-(2-ethylxanthogenphenylacetyl)glycine,

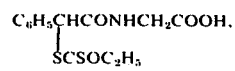

as white crystals. (m.p. 133° - 135.5°C)
Infrared Spectrum:
1055 cm$^{-1}$ (xanthate);

By the hydrolysis of the thus obtained xanthate, N-(2-mercaptophyenylacetyl)glycine mentioned in Example I could readily be obtained.

EXAMPLE III 60.5g of 2-bromo-3-phenylpropionic acid was mixed with 100 ml of thionylchloride and the mixture was refluxed for 3 hours and, after the excess thionylchloride had been distilled off, was distilled under reduced pressure to give 46.2g of 2-bromo-3-phenylpropionylchloride. (b.p. 100°– 101°C/4 mmHg)

60g of 2-bromo-3-phenylpropionylchloride was added dropwise to the solution which had been prepared by dissolving 21.8g of glycine and 19.4g of NaOH in 250 ml of water over 1 hour while stirring and ice-cooling. After completion of the addition, the mixture was stirred at room temperature for additional 4 hours. The mixture was maintained at a pH of 8 during the reaction. After completion of the reaction, the reaction mixture was acidified with hydrochloric acid to form 70.9g of 2-bromo-3-phenylpropionylglycine having a melting point of 148°C after recrystallization from ethyl acetate.

The thus formed bromine-containing compound was reacted with 43.2g of thiobenzoic acid in a similar way in accordance with Example I to give 85.0g of 2-benzoylmercapto-3-phenylpropionylglycine which had a melting point of 181° – 182°C after recrystallization from ethylacetate-ethanol.

The thus obtained compound was hydrolized in a concentrated aqueous ammonia solution in a manner similar to that used in Example I to give N-(2-mercapto-3-phenylpropionyl)glycine, $C_6H_5CH_2CH(SH)CONHCH_2COOH$, (m.p. 122° – 125°C) at a yield of 81%. After recrystallization from ethyl acetate, the compound had a melting point of 126° – 127°C and was 100% pure as determined by iodometry.

Infrared Spectrum:
3260 $cm^{-1}$ (—NH—); 1720 $cm^{-1}$ (—COOH); 1635 $cm^{-1}$, 1560 $cm^{-1}$ (—CONH—)

When L-2-bromo-3-phenylpropionic acid was used as a starting material, optically active N-(2-mercapto-3-phenylpropionyl)glycine was obtained. (m.p. 55° – 58°C, $[\alpha]_D^{36} = -5.3°$).

Infrared Spectrum:
3260 $cm^{-1}$ (—NH—); 1710 $cm^{-1}$ (—COOH); 1635 $cm^{-1}$, 1550 $cm^{-1}$ (—CONH—)

EXAMPLE IV 28.3g (0.113 mol) of 2-bromo-p-chlorophenylacetic acid was mixed with 26.9g (0.226 mol) of thionylchloride and the mixture was refluxed for 2.5 hours. After the excess thionylchloride had been distilled off, the reaction mixture was distilled under reduced pressure to give 26.7g of 2-bromo-p-chlorophenylacetyl chloride as yellow-orange oil. (b.p. 148° – 152°C/15 mmHg)

4.9g (0.065 mol) of glycine was dissolved in 250 ml of 0.5 N—NaOH and then to the solution was added dropwise 14.6g (0.054 mol) of 2-bromo-p-chlorophenylacetyl chloride over 1 hour while stirring and cooling with a freezing mixture. After completion of the addition, the reaction mixture was stirred at room temperature for an additional 2 hours. During stirring, the pH of the mixture was adjusted to 8. The filtrate which had been prepared by dissolving 11.6g (0.08 mol) of thiobenzoic acid in 40 ml of 2N—KOH and filtering the solution to remove undissolved substances was added to the reaction mixture followed by stirring at room temperature overnight. The next morning, the mixture was acidified with hydrochloric acid while ice-cooling to precipitate crystals. These crystals were recovered by filtration, washing with water and washing with benzene to give 15.1g of crude N-(2-benzoylmercapto-p-chlorophenylacetyl)glycine. The product had a melting point of 158° – 159°C after recrystallization from ethyl acetate-benzene. 11.0g (0.03 mol) of N-(2-benzoylmercapto-p-chlorophenylacetyl)glycine was dissolved in 75 ml of concentrated aqueous ammonia followed by stirring at room temperature for 1 hour. After removal of benzamide by extraction with ethyl acetate, the resulting aqueous layer was treated in a similar manner in accordance with Example I to give 6.0g of N-(2-mercapto-p-chlorophenylacetyl)glycine, $ClC_6H_4CH(SH)—CONHCH_2COOH$. (m.p. 148° – 149°C, Purity; 100% (iodometry))

Infrared Spectrum:
3260 $cm^{-1}$ (—NH—); 1760 $cm^{-1}$ (—COOH); 1610 $cm^{-1}$, 1540 $cm^{-1}$ (—CONH—)

EXAMPLE V 50g of 2-bromoisovaleric acid was mixed with 80 ml of thionylchloride and the mixture was refluxed for 4 hours to give 45.9g of 2-bromoisovaleryl chloride. (b.p. 68° – 70°C/29 mmHg)

50.1g of the resulting valerylchloride and 10g of triethylamine were added dropwise over one hour to the solution, which had been prepared by neutralizing 18.8g (0.25 mol) of glycine with 10.0g of NaOH in 100 ml of water, while stirring and ice-cooling and followed by stirring at room temperature for an additional one hour. Then the mixture was acidified with hydrochloric acid to give 51.6g of 2-bromoisovalerylglycine. (m.p. 138° – 139°C).

In a manner similar to that used in any one of the foregoing Examples 27.5g (0.116 mol) of 2-bromoisovalerylchloride was reacted with 20.6g (0.15 mol) of thiobenzoic acid by stirring at room temperature for 40 hours. After completion of the reaction, the reaction mixture was acidified with hydrochloric acid to give 29.0g of 2-benzoylmercaptoisovalerylglycine having a melting point of 136° – 137°C after recrystallization from ethyl acetate.

Infrared Spectrum:
3360 $cm^{-1}$ (—NH—); 1735, 1215, 920 $cm^{-1}$ (benzoate);
1650 $cm^{-1}$ (—COOH); 1615, 1540 $cm^{-1}$ (—CONH—)

In a manner similar to that used in Example I, N-(2-benzoymercaptoisovaleryl)glycine was hydrolized with concentrated aqueous ammonia to give N-(2-mercaptoisovaleryl)glycine, $(CH_3)_2CHCH(SH)CONHCH_2COOH$ having a melting point of 118° – 119°C after recrystallization from ethyl acetatebenzene.

Infrared Spectrum: 3280 $cm^{-1}$ (—NH—); 2500 $cm^{-1}$ (—SH); 1750 $cm^{-1}$ (—COOH); 1605, 1560 $cm^{-1}$ (—CONH—)

EXAMPLE VI 33g (0.20 mol) of DL-phenylalanine was neutralized with 100 ml of 2N-NaOH solution and to the resulting solution were simultaneously added dropwise 34.2g (0.20 mol) of 2-bromo-propionylchloride and 110 ml of 2N-NaOH solution over about one hour while stirring and ice-cooling. During the reaction, the reaction mixture was maintained in a slightly alkaline condition. After completion of the addition, the ice-bath was removed and the mixture was stirred at room temperature for a further 2 hours. The filtrate which had been prepared by neutralizing 33.7g (0.24 mol) of thiobenzoic acid with 122 ml of 2N—KOH solution and filtering the thus obtained solution was added to the reaction mixture. The mixture was stirred at room temperature overnight and then acidified with hydrochloric acid while ice-cooling to form oil. The oil was extracted with ethyl acetate and the extract was washed with water, dried over anhydrous sodium sulfate, and then allowed to be placed under reduced pressure to remove the ethyl acetate. During removal of the ethyl acetate, crystals started to precipitate. After completion of the evaportion, benzene was added to these crystals and they were recovered by filtration and washed with benzene to give 25.0g of N-(2-benzoylmercaptopropionyl)phenylalanine. (m.p. 173° – 175°C)

Infrared Spectrum:

3240 cm⁻¹ (—NH—); 1710 cm⁻¹ (—COOH); 1630, 1540 cm⁻¹ (—CONH—); 915 cm⁻¹ (S-benzoate)

The filtrate obtained above was concentrated to give 31.8g of crystals which had a melting point of 99° – 103°C after recrystallization from ethyl acetate-benzene.

Infrared Spectrum:
3380 cm⁻¹ (—NH—); 1740 (Shoulder), 1720 cm⁻¹ (—COOH); 1650, 1510 cm⁻¹(—CONH—); 910 cm⁻¹ (S-benzoate)

Thus, two types of crystals (crystals of a higher melting point and those of a lower melting point) were obtained by separation of diastereoisomers. Each type of crystals was hydrolized in a similar manner according to Example I to give N-(2-mercaptopropionyl-phenylalanine,

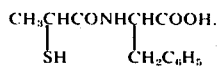

The compound of a higher melting point (m.p. 131° – 132°C)
Infrared Spectrum:
3320 cm⁻¹ (—NH—); 1715 cm⁻¹ (—COOH); 1620, 1525 cm⁻¹ (—CONH—)
Analysis:
Found: C, 57.00; H, 6.01; N, 5.54;
Calcd.: C, 56.81; H, 5.97; N, 5.33

The compound having a lower melting point (m.p. 105° – 108°C)
Infrared Spectrum:
3300 cm⁻¹ (—CONH—); 1705 cm⁻¹(—COOH); 1625 cm⁻¹, 1525 cm⁻¹(—CONH—)
Analysis:
Found: C, 57.17; H, 6.06; N, 5.54
Calcd.: C, 56.81; H, 5.97; N, 5.53

EXAMPLE VII 13.1g (0.10 mol) of DL-leucine was neutralized with 50 ml of 2N-NaOH solution and to the solution were simultaneously added dropwise 17.1g (0.10 mol) of 2-bromopropionylchloride and 50 ml of 2N-NaOH solution at room temperature over one hour while stirring and maintaining the reaction mixture in a slightly alkaline condition. After completion of the addition, the ice bath used was removed and the mixture was stirred at room temperature for 3 hours. Successively, to the mixture was added the filtrate which had been prepared by neutralizing 13.8g (0.10 mol) of thiobenzoic acid with 50 ml of 2N—KOH solution and filtering. The resulting mixture was stirred at room temperature overnight and then acidified with hydrochloric acid to form oil. After extraction of oil with ethyl acetate, the oil was purified by subjecting it to chromatography using a silica gel column to give 18.5g of N-(2-benzoylmercaptopropionyl)leusine as oil. 40 ml of concentrated aqueous ammonia was added to 6.0g of N-(2-benzoylmercaptopropionyl)leucine to allow the derivative of leucine to hydrolyze in a manner similar to that used in Example I to give 2.6g of N-(2-mercaptopropionyl)leucine,

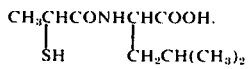

(m.p. 77° – 84°C)
Analysis:

Found: C, 49.54; H, 7.94; N, 6.68;
Calcd.: C, 49.30; H, 7.82; N, 6.39.

EXAMPLE VIII 8.9g (0.10 mol) of β-alanine was dissolved in 100 ml of water. To the solution was added 20 ml of triethylamine and then was added dropwise 22.2g (0.13 mol) of 2-bromopropionylchloride over one hour while stirring and ice-cooling. The mixture was stirred for a further 2 hours. To the mixture was added the filtrate which had been prepared by neutralizing 19.5g (0.14 mol) of thiobenzoic acid with an aqueous KOH and filtering the solution, followed by stirring overnight. Crystals precipitated were recovered by filtration, washed with water and dried to give 20.8g of N-(2-benzoylmercaptopropionyl-β-alanine. After recrystallization from benzene, the product had a melting point of 94° – 97°C.

Infrared Spectrum: 3240 cm⁻¹(—NH—); 1645 cm⁻¹, 1545 cm⁻¹(—CONH—); 910 cm⁻¹(S-benzoate)

22.5g (0.08 mol) of N-(2-benzoylmercaptopropionyl-β-alanine was added to the solution of 10.0g (0.25 mol) of NaOH in 100 ml of water to allow the β-alanine derivative to hydrolyze at 40°C for 1 hour. The reaction mixture was acidified with hydrochloric acid and, after distilling off the benzoic acid, concentrated to give 8.8g of N-(2-mercaptopropionyl-βalanine,

The product had a melting point of 100° – 103°C, after recrystallization from ethyl acetate.
Infrared Spectrum: 3250 cm⁻¹(—NH—); 1700 cm⁻¹ (—COOH); 1635 cm⁻, 1560 cm⁻¹(—CONH—).
Analysis: Found: C, 40.50; H, 6.29; N, 7.96; Calcd.: C, 40.68; H, 6.26; N, 7.91.

EXAMPLE IX 50g (0.383 mol) of 5-aminocaproic acid was added to 200 ml of water and 10 ml of pyridine was added to the solution. Then, the acid was reacted with 66.5g (0.383 mol) of 2-bromo-propionylchloride and 52.9g (0.383 mol) of thiobenzoic acid in the same manner as described in Example VIII to give, after extraction with diethyl ether, N-(2-benzoylmercaptopropionyl)-5-amino-caproic acid as viscous residue.

Infrared Spectrum: 3280 cm⁻¹ (—NH—); 1660 cm⁻¹, 1530 cm⁻¹ (—CONH—); 1720 cm⁻¹(—COOH); 910 cm⁻¹(S-Benzoate)

12.4g of N-(2-benzoylmercaptopropionyl)-5-aminocaproic acid was hydrolized with NaOH in a similar manner as described in Example VIII to give 5.2g of N-(2-mercaptopropionyl)-5-aminocaproic acid,

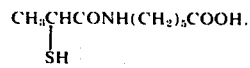

(m.p. 78° – 79°C)
Infrared Spectrum; 3240 cm⁻¹(—NH—); 1695 cm⁻¹ (—COOH); 1630 cm⁻¹, 1560 cm⁻¹(—CONH—)
Analysis: Found: C, 4926; H, 7.78; N, 6.42; Calcd.: C, 49.30; H, 7.82; N, 6.39.

EXAMPLE X 82.0g (0.54 mol) of DL-phenylglycine was neutralized by dissolving it with 720 ml of 2N—NaOH aqueous solution. 93.1g (0.54 mol) of 2-bromopropionylchloride and 720 ml of 2N—NaOH aqueous solution was simultaneously added dropwise to the solution over 1 hour while stirring and ice-cooling. During the addition, the reaction system was maintained in a slightly alkaline condition. After completion of the addition, the ice bath was removed and the mixture was stirred for further 2 hours. Then, the mixture was acidified with hydrochloric acid to precipitate crystals. The crystals thus formed were recovered by filtration, washed with water and dried to give 147.3g of N-(2-bromopropionylphenyl)glycine. (m. p. 144° – 147°C; Yield, 94.8%)

Infrared Spectrum: 3200 cm$^{-1}$(—NH—); 1720 cm$^{-1}$(—COOH); 1630 cm$^{-1}$, 1520 cm$^{-1}$(—CONH—).

111g (0.39 mol) of 2-bromopropionylphenylglycine thus obtained was dissolved in 194 ml of 2N-NaOH aqueous solution. To the solution was added the filtrate, which had been prepared by neutralizing 58.9g (0.43 mol) of thiobenzoic acid with 214 ml of 2N—NaOH aqueous solution and filtering the neutralized solution, and followed by stirring overnight. On the next morning, the reaction mixture was acidified with hydrochloric acid to form oil. The oil was extracted with ethyl acetate, and the extract was dried over ahydrous sodium sulfate and distilled under reduced pressure to remove ethyl acetate to give 129g of crystals. These crystals were recovered by filtration and washed with benzene to give 83.8g of N-(2-benzoylmercaptopropionylphenyl)glycine. (m.p. 149° – 151°C; Yield, 62.9%)

Infrared Spectrum: 3280 cm$^{-1}$(—NH—); 1720 cm$^{-1}$(—COOH); 1630 cm$^{-1}$, 1520 cm$^{-1}$(—COHN—)

To 34.3g (0.1 mol) of the S-benzoyl compound thus obtained was added 170 ml of aqueous ammonia thereby hydrolyzing the compound in the manner similar to that described in Example I to give 20.1g of N-(2-mercaptopiopionyl)phenylglycine,

(m.p. 135° – 136°C; Yield, 84.1%)
Infrared Spectrum: 3260 cm$^{-1}$(—NH—); 1700 cm$^{-1}$(—COOH); 1635 cm$^{-1}$, 1525 cm$^{-1}$(—CONH—).
Analysis: Found: C, 55.17; H, 5.43; N, 5.62. Calcd.: C, 55.23; H, 5.48; N, 5.86.

We claim:
1. N-(2-mercaptopropionyl)β-alanine.
2. N-(2-mercaptopropionyl)5-aminocaproic acid.

* * * * *

UNITED STATES PATENT AND TRADEMARK OFFICE
CERTIFICATE OF CORRECTION

PATENT NO. : 3,971,828
DATED : July 27, 1976
INVENTOR(S) : ITARU MITA et al

It is certified that error appears in the above-identified patent and that said Letters Patent are hereby corrected as shown below:

Column 2, in the Table: after "N-(2-mercaptoisovaleryl)-"

delete "20.0", "(10)" and "0.92";

insert --- 20.0 --- under the heading "Percent of mice...";

insert --- (10) --- under the heading "Dose";

insert --- 0.92 --- under the heading "Partition coefficient...".

Column 5, line 20: after "1720 $cm^{-1}$", insert

--- 1705 $cm^{-1}$ --- before "(-COOH)".

Column 7, line 16: after "(2-mercaptopropionyl", insert --- ) ---.

Column 7, line 38: after "5.53", delete "EXAMPLE VII";

before the next paragraph, insert -- EXAMPLE VII -- as the heading.

UNITED STATES PATENT AND TRADEMARK OFFICE
CERTIFICATE OF CORRECTION

PATENT NO. : 3,971,828

DATED : July 27, 1976

INVENTOR(S) : ITARU MITA et al

Page 2 of 2

It is certified that error appears in the above-identified patent and that said Letters Patent are hereby corrected as shown below:

Column 8, line 16: after "zoylmercaptopropionyl", replace "-" with --- ) ---.

Column 8, line 23: after "nyl" and before "β-alanine", replace "-" with --- ) ---.

Column 8, line 28: replace "propionyl-βalanine" with --- propionyl)β-alanine ---.

Column 9, line 21: after "2-bromopropionylphenyl" and before "glycine", insert --- ) ---.

Signed and Sealed this

Twenty-ninth Day of March 1977

[SEAL]

Attest:

RUTH C. MASON
*Attesting Officer*

C. MARSHALL DANN
*Commissioner of Patents and Trademarks*